US008834170B2

(12) United States Patent
Kurenov et al.

(10) Patent No.: US 8,834,170 B2
(45) Date of Patent: Sep. 16, 2014

(54) DEVICES AND METHODS FOR UTILIZING MECHANICAL SURGICAL DEVICES IN A VIRTUAL ENVIRONMENT

(75) Inventors: Sergei N. Kurenov, West Falls, NY (US); Juan Carlos Cendan, Gainesville, FL (US); Jorg Peters, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1161 days.

(21) Appl. No.: 12/446,587

(22) PCT Filed: Nov. 3, 2007

(86) PCT No.: PCT/US2007/083550
§ 371 (c)(1),
(2), (4) Date: Oct. 16, 2009

(87) PCT Pub. No.: WO2008/058039
PCT Pub. Date: May 15, 2008

(65) Prior Publication Data
US 2010/0291520 A1    Nov. 18, 2010

Related U.S. Application Data

(60) Provisional application No. 60/857,237, filed on Nov. 6, 2006.

(51) Int. Cl.
*G09B 23/28* (2006.01)
(52) U.S. Cl.
USPC ........................................... 434/262

(58) Field of Classification Search
CPC .............................. G09B 230/00; G09B 23/28
USPC ........................................................ 434/262
See application file for complete search history.

(56) References Cited

U.S. PATENT DOCUMENTS

| 5,149,270 A | 9/1992 | McKeown |
| 5,403,191 A | 4/1995 | Tuason |
| 5,478,344 A | 12/1995 | Stone et al. |
| 5,478,345 A | 12/1995 | Stone et al. |

(Continued)

FOREIGN PATENT DOCUMENTS

| JP | 5303327 | 11/1993 |
| JP | 2004-0344491 | 12/2004 |

(Continued)

OTHER PUBLICATIONS

Brown et al., "Real-time knot-tying simulation," *The Visual Computer*, 2004, vol. 20, pp. 165-179.

(Continued)

*Primary Examiner* — Kesha Frisby
(74) *Attorney, Agent, or Firm* — Saliwanchik, Lloyd & Eisenschenk

(57) ABSTRACT

Devices and methods that combine an actual surgical instrument handle, for example the handle of an AutoSuture EndoStitch™ device, with a force feedback generator able to create resistance to motion similar to that encountered in a real operating environment. The devices and methods provide a means for repeatedly performing maneuvers that accurately simulate the actual instrument, but in a virtual environment. The devices have haptic capabilities and collision detection so that the virtual device, such as the needle driver of the EndoStitch™ device, is "aware" of instrument contact.

25 Claims, 16 Drawing Sheets

(56) References Cited

U.S. PATENT DOCUMENTS

| | | | |
|---|---|---|---|
| 5,480,406 | A | 1/1996 | Nolan et al. |
| 5,503,149 | A | 4/1996 | Beavin |
| 5,766,016 | A | 6/1998 | Sinclair et al. |
| 5,800,179 | A | 9/1998 | Bailey |
| 6,038,488 | A | 3/2000 | Barnes et al. |
| 6,062,865 | A | 5/2000 | Bailey |
| 6,088,020 | A | 7/2000 | Mor |
| 6,113,395 | A * | 9/2000 | Hon .............................. 434/262 |
| 6,369,834 | B1 | 4/2002 | Ziles et al. |
| 6,377,011 | B1 | 4/2002 | Ben-Ur |
| 6,396,232 | B2 | 5/2002 | Haanpaa et al. |
| 6,417,638 | B1 | 7/2002 | Guy et al. |
| 6,529,183 | B1 | 3/2003 | MacLean et al. |
| 6,697,043 | B1 | 2/2004 | Shahoian |
| 6,810,281 | B2 | 10/2004 | Brock et al. |
| 6,857,878 | B1 | 2/2005 | Chosack et al. |
| 6,863,536 | B1 | 3/2005 | Fisher et al. |
| 6,924,787 | B2 | 8/2005 | Kramer et al. |
| 6,939,138 | B2 | 9/2005 | Chosack et al. |
| 6,985,133 | B1 | 1/2006 | Rodomista et al. |
| 6,991,627 | B2 | 1/2006 | Madhani et al. |
| 7,023,423 | B2 | 4/2006 | Rosenberg |
| 7,056,123 | B2 | 6/2006 | Gregorio et al. |
| 7,236,618 | B1 | 6/2007 | Chui et al. |
| 7,261,565 | B2 | 8/2007 | Chosack et al. |
| 7,289,106 | B2 | 10/2007 | Bailey et al. |
| 2003/0210259 | A1 | 11/2003 | Liu et al. |
| 2005/0118557 | A1 | 6/2005 | Sumner, II et al. |
| 2005/0142525 | A1* | 6/2005 | Cotin et al. ................... 434/262 |
| 2005/0181340 | A1 | 8/2005 | Haluck |
| 2005/0214727 | A1 | 9/2005 | Stoianovici et al. |
| 2005/0221263 | A1 | 10/2005 | Vecerina et al. |
| 2005/0277096 | A1 | 12/2005 | Hendrickson et al. |
| 2006/0073454 | A1 | 4/2006 | Hyltander et al. |
| 2007/0035511 | A1 * | 2/2007 | Banerjee et al. |
| 2007/0172803 | A1* | 7/2007 | Hannaford et al. ........... 434/262 |
| 2007/0207448 | A1 | 9/2007 | Glaser et al. |
| 2007/0275359 | A1 | 11/2007 | Rotnes et al. |
| 2009/0253109 | A1* | 10/2009 | Anvari et al. ................. 434/262 |

FOREIGN PATENT DOCUMENTS

| | | |
|---|---|---|
| WO | WO 01-84530 | 11/2001 |
| WO | WO 2007-068050 | 6/2007 |
| WO | WO 2007-121572 | 11/2007 |
| WO | WO 2008-033541 | 3/2008 |
| WO | WO 2008-058039 | 5/2008 |

OTHER PUBLICATIONS

Hubbard, "Collision Detection for Interactive Graphics Applications," *IEEE Transactions on Visualization and Computer Graphics*, Sep. 1995, vol. 1, No. 3, pp. 218-230.

Kim et al., "Exploiting graphics hardware for haptic authoring," *Proceedings of Medicine Meets Virtual Reality 14*, Long Beach, CA, Jan. 25-27, 2006, vol. 119, pp. 255-260.

Kurenov et al., "Simulation for Training with Autosuture™ Endo Stitch™ Device," *Surg Innov*, Dec. 2006, vol. 13, No. 4, pp. 283-287.

Lenoir et al., "Surgical thread simulation," *ESAIM: Proceedings*, Nov. 2002, vol. 12, pp. 102-107.

Pattaras et al., "Comparison and Analysis of Laparoscopic Intracorporeal Suturing Devices: Preliminary Results," *Journal of Endourology*, Mar. 2001, vol. 15, pp. 187-192.

Phillips et al., "Simulated knot tying," *IEEE International Conference on Robotics and Automation*, 2002, pp. 841-846.

Tan et al., "Evaluation of a Novel Modified Suture Material Designed to Facilitate Intracorporeal Knot Tying during Laparoscopic Surgery," *Journal of Endourology*, Nov. 2005, vol. 19, pp. 1104-1108.

Wang et al., "Dynamic thread for real-time knot tying," *IEEE Computer Society*, 2005, pp. 507-508.

O'Toole, R.V. et al., "Measuring and Developing Suturing Technique with a Virtual Reality Surgical Simulator," *J. Am Coll Surg*, 1999, pp. 114-127, vol. 189, No. 1.

Webster, R.W. et al., "A Prototype Haptic Suturing Simulator," *Medicine Meets Virtual Reality*, 2001, pp. 567-569.

Larsson, A., "Intracorporeal Suturing and Knot Tying in Surgical Simulation," *Medicine Meets Virtual Reality*, 2001, pp. 266-271.

Lenoir, J. et al., "Surgical Thread Simulation," *ESAIM: Proceedings*, Nov. 2002, pp. 102-107, vol. 12.

Lim, K.M. et al., "Multi-Scale Simulation for Microsurgery Trainer," *Proceedings of the 2004 IEEE International Conference on Robotics & Automation*, Apr. 2004, pp. 1215-1220, New Orleans, LA.

Leduc, M. et al., "Toward Modeling of a Suturing Task," *Proceeding Graphics Interface*, Jun. 11-13, 2003, pp. 273-278, Halifax, Nova Scotia.

Lindblad, A.J. et al., "Two-Handed Next Generation Suturing Simulator," *Medicine Meets Virtual Reality*, 2004, pp. 215-220, ISO Press.

Holbrey, R. et al., "A Model for Virtual Suturing in Vascular Surgery," *Proceedings of the Theory and Practice of Computer Graphics*, 2004, IEEE.

Wang, F. et al., "Dynamic thread for real-time knot-tying," *Proceedings of the First Joint Eurohaptics Conference and Symposium on Haptic Interfaces for Virtual Environment and Teleoperator Systems*, 2005, IEEE.

Marshall, P. et al., "A Study on Haptic Rendering in a Simulated Surgical Training Environment," *Symposium on Haptic Interfaces for Virtual Environment and Teleoperator Systems*, Mar. 25-26, 2006, pp. 241-247, Alexandria, VA, IEEE.

Basdogan, C. et al., "Haptics in Minimally Invasive Surgical Simulation and Training," *IEEE Computer Graphics and Applications*, Mar./Apr. 2004, pp. 56-64, vol. 24, No. 2.

Dutta, S. et al., "Simulation: A New Frontier in Surgical Education," *Advances in Surgery*, 2006, pp. 249-263, vol. 40.

Harrington, D.T. et al., "A Time-Cost Analysis of Teaching a Laparoscopic Entero-Enterostomy," *Journal of Surgical Education*, 2007, pp. 342-345, vol. 64, No. 6.

Liu, A. et al., "A Survey of Surgical Simulation: Applications, Technology, and Education," *Presence: Teleoperators and Virtual Environments*, Dec. 2003, pp. 599-614, vol. 12, No. 6.

Scott, D.J. et al., "The Changing Face of Surgical Education: Simulation as the New Paradigm," *Journal of Surgical Research*, 2008, pp. 189-193, vol. 147, No. 2.

True Assessment Systemt™ (TAS), http://www.e-trinsic.com/secondary_template.asp?section=prodserv&page=assessment, 2002, pp. 1-2.

Ethicon Endo-Surgery, "REALIZE™ Adjustable Gastric Band Product Insert," obtained Dec. 2007, pp. 1-25.

Ethicon Endo-Surgery, "REALIZE™ Adjustable Gastric Band Patient Guide," obtained Dec. 2007, pp. 1-40.

SensAble Technologies Stylus Adaptor Kit for PHANTOM® Desktop™ Haptic Device product brochure [online, .pdf, retrieved Apr. 22, 2009] retrieved from: http://www.sensable.com/documents/documents/Stylus_Adaptor_Kit_for_Phantom_Desktop.pdf, p. 1.

Simbionix™ Gastric Bypass Module product information [online, webpage, retrieved Sep. 4, 2008] retrieved from: http://simbionix.com/Lap-mentor/LAP_modules_Gastric_Bypass.html, p. 1.

Simbionix™ Suturing Modules product information [online, webpage, retrieved Sep. 4, 2009] retrieved from: http://simbionix.com/Lap_mentor/LAP_Modules_Suturing.html, p. 1.

Simbionix™ product brochure [online, .pdf, retrieved Sep. 17, 2008] retrieved from: http://simbionix.com/wp-content/uploads/2011/01/LAPBrochure08-2012-Web.pdf, pp. 1-2.

Simbionix™ Rehearsal Studio Procedure product information [online, .pdf, retrieved Sep. 4, 2008] retrieved from: http://www.simbionix.com/PROcedure.html, pp. 1-3.

Simbionix™ Lap Mentor product information [online, .pdf, retrieved Sep. 17, 2008] retrieved from: http://www.simbionix.com/LAP_Platforms.html, pp. 1-2.

Simbionix™ Angio Mentor™ product information [online, .pdf, retrieved Sep. 17, 2008] retrieved from: http://www.simbionix.com/ANGIO_Mentor.html, pp. 1-2.

(56) References Cited

OTHER PUBLICATIONS

Simbionix™ GI Mentor II™ product information [online, .pdf, retrieved Sep. 17, 2008] retrieved from: http://www.simbionix.com/GI_Mentor.html, pp. 1-2.
Simbionix™ URO Mentor™ product information [online, .pdf, retrieved Sep. 17, 2008] retrieved from: http://www.simbionix.com/URO_Mentot.html, p. 1.

Simbionix™ PERC Mentor™ product information [online, .pdf, retrieved Sep. 4, 2008] retrieved from: http://www.simbionix.com/PERC_Mentor.html, p. 1.

Simbionix™ Laparoscopic Instruments product information [online, .pdf, retrieved Sep. 4, 2008] retrieved from: http://www.simbionix.com/LAP_Laparoscopic_Instruments.html, p. 1.

* cited by examiner

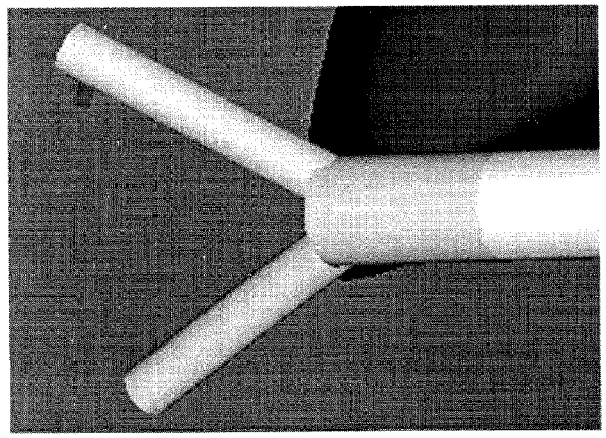
FIG. 10A
FIG. 10B
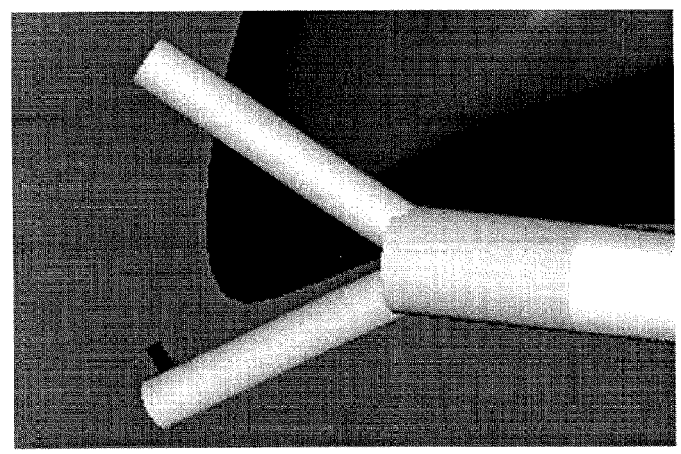
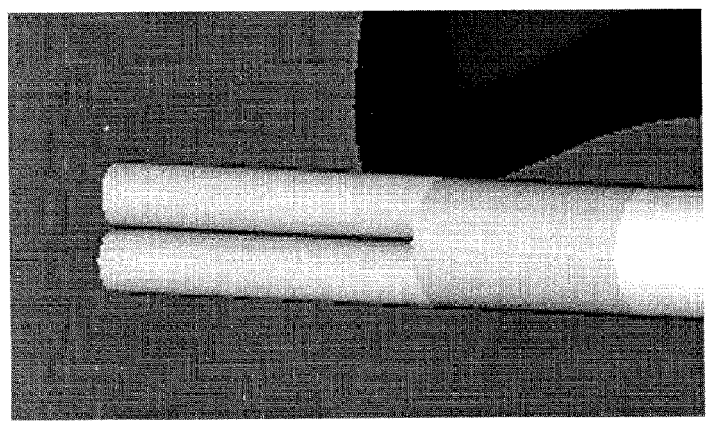
FIG. 10C

1. Initialize modeling environment;
   Generate virtual objects:
   – instrument tip
   – needle
   – suture
   – jaws 2. Simulate Instrument Tip with the Needle.
Needle position depends on the Handle status: a) squeezed, b) unsqueezed – modeled with switch #1(SW1):
   – squeezed - SW1 = False (open)
   – unsqueezed - SW1 = True (closed)
And, also, depends on Sliding Lever position – modeled with switches #2 and #3 (SW2; SW3):
   – SW2 = True (closed) needle in Left jaw;
   – SW3 = True (closed) needle in Right jaw;

Pseudo code:

```
IF SW1 = False, THEN
        Display jaw Closed, needle between jaws
ELSE
        IF SW1 = True AND SW2 = True, THEN
                Display jaw Open, needle in Left jaw
        ELSE
                IF SW1 = True AND SW3 = True, THEN
                        Display jaw Open, needle in Right jaw
        END IF
END IF
```

FIG. 15A

DEVICES AND METHODS FOR UTILIZING MECHANICAL SURGICAL DEVICES IN A VIRTUAL ENVIRONMENT

CROSS REFERENCE TO RELATED APPLICATION

This application is a National Stage Application of International Application Number PCT/US2007/083550, filed Nov. 3, 2007; which claims the benefit of U.S. provisional patent application Ser. No. 60/857,237, filed Nov. 6, 2006, which are hereby incorporated by reference in their entirety.

BACKGROUND OF INVENTION

Laparoscopic surgeries often require the closing of wounds with sutures that require tying knots. However, with laparoscopic instruments in an intracorporeal environment, tying knots can be a challenging and time-consuming process.

Several suturing devices have been developed that can reduce or eliminate the difficulties and time involved with tying knots in laparoscopic surgeries. However, the rapid development and deployment of novel minimally invasive instruments presents the surgical educator with a significant challenge. For example, the AutoSuture™ EndoStitch™ device (US Surgical/Tyco) has been shown to reduce the time required for tying knots and produces knots of comparable, if not greater, strength than standard laparoscopic knot tying techniques. (Pattaras, John G., et al., "Comparison and Analysis of Laparoscopic Intracorporeal Suturing Devices: Preliminary Results", J. Endourology 2001, 15:187-192). The mechanisms and techniques of operation for the EndoStitch™ device are detailed in U.S. Pat. Nos. 5,478,344; 5,478, 345; and 5,480,406. However, these devices often require skills significantly different from those used for conventional surgical knot tying. As such, there can be a significant learning curve involved in developing the skills necessary to efficiently and effectively use new devices. (Tan, Andrew et al., J. Endourology 2005, 19(9):1104-1108). This is unacceptable in today's environment: throughput pressures in the operating room leave little room for delays or even minor mistakes.

In order to achieve proficiency, surgeons must be instructed and spend time using these suturing devices, or any other new instrumentation. However, maximizing trainee proficiency in a limited amount of time, while ensuring patient safety, has also proven to be very challenging. A variety of methods can be used for such practice, including anatomically correct models, videoscopic trainers, or, more realistic conditions, i.e., within excised organs, cadavers, or living animals. However, such practice requires time and in some circumstances travel by the surgeon to a practice site. In addition, actual suturing devices are often used during training. Many of the suturing devices are expensive and single-patient use, meaning that they must be properly disposed of after use on a single patient, or after a single practice session, and cannot be re-sterilized. As result, practice sessions with the actual devices can also be expensive since they must often be disposed of after each practice session.

Virtual environments have also been developed that simulate surgical environments in which surgeons can "practice" various techniques and instruments. Some of these virtual environments have also utilized haptic feedback devices (SensAble Technologies, Woburn, Mass.) to simulate the feel of touching or interacting with real tissues or organs. (Kim, M., Punak, S., Cendan, J., Kurenov, S., and Peters, J. 2006. Exploiting graphics hardware for haptic authoring. *Proceedings of Medicine Meets Virtual Reality (MMVR)* 14, Jan. 25-27, 2006, Long Beach, Calif., IOS Press, Amsterdam, Studies in Health Technology and Informatics (SHTI), 2006; 119:255-260; Hubbard, P. Collision Detection for Interactive Graphics Applications. *IEEE Transactions on Visualisation and Computer Graphics*. 1995; 1, No 3:218-230). Therefore, a need exists for a more convenient and less time-consuming way for surgeons to develop the necessary skills to efficiently utilize surgical devices, particularly laparoscopic suturing devices. A further need exists to reduce or eliminate the on-going expense of using multiple surgical devices in practice sessions.

BRIEF SUMMARY

The subject invention provides systems and methods for surgical education and training, but the embodiments disclosed are not limited thereto. In embodiments of the subject invention, a 3-dimensional interactive environment that allows a user to interface with one or more computers using modified surgical instruments, or portions thereof, as end effectors or input devices is provided. According to the subject invention, the modified surgical instruments and interactive environment are capable of retaining the specific look and feel of the actual surgical instruments while interacting with a computer, for surgical education and training.

Specifically exemplified in the subject invention are realistic and efficient simulations of an environment that incorporate a model of the actual instrument working tip which can be manipulated by the modified real handle of a surgical instrument. Embodiments of the system of subject the invention utilize actual surgical instruments that have been modified for attachment to haptic devices making it possible for surgeons to develop surgical skills and techniques by touching and manipulating devices and objects within computerized, 3 dimensional, real-time virtual environments.

In one embodiment, the subject invention provides laparoscopic suturing instruments that have been modified for attachment to haptic devices, which allows surgeons to develop knot-tying or other skills in virtual environments where they can touch and manipulate the virtual devices and virtual tissues.

Appropriate software can further simulate realistic intracorporeal or in vivo environments on a computer monitor providing surgeons with a more realistic training and/or teaching environment. Utilizing the haptic surgical devices, surgeons are able to manipulate the controls, levers, switches, etc. of haptic surgical devices and view the effects of their actions in real-time on a computer monitor or other viewing apparatus. Thus, for example, surgeons can practice tying "virtual knots" on virtual intracorporeal tissues utilizing the haptic surgical devices at any convenient time or place. Further, because the device and tissues are virtual, it is not necessary to utilize and dispose of "real" suturing devices for each practice session.

In a specific embodiment, the subject invention provides a system having an AutoSuture EndoStitch™ laparoscopic suturing device (US Surgical/Tyco) that has been modified for attachment to a Phantom® Omni haptic device (SensAble Technologies). In this embodiment, surgeons are able to manipulate the controls of the haptically enhanced surgical EndoStitch™ device and view the effects of their actions on the virtual working tip of the EndoStitch™ device, which is viewable on a computer monitor.

The Stylus Adapter Kit for the PHANTOM® Desktop™ Haptic Device (SensAble Technologies, Woburn, Mass.) allows the attachment of a variety of devices for medical applications such as laparoscopy instruments, dental tools, and other types of tools to the PHANTOM Desktop stylus. However, for novel devices like the Autosuture Endostich™ (US Surgical, Norwalk, Conn.), the specific and uncommon manipulations required at the handle do not match the interaction anticipated for the PHANTOM Adapter Kit. Moreover such uncommon manipulation at the handle must be transferred into a computer model. Specifically, the needle movement between the jaws of the Endostich™ device during the knot tying procedure requires a complex manipulation, which can be difficult to learn.

The subject invention provides a system of software and hardware developed to provide a computer model of a surgical device, or portion thereof, with realistic hand feel and haptic feedback that can simulate the experience of a "real" surgical procedure when utilizing a particular surgical instrument. Particularly exemplified is the adaptation of an instrument handle as an end effecter or input device for a computer simulation.

In addition, the subject invention utilizes software that can simulate 3-dimensional virtual tissues or other objects. In particular, the subject application discloses a model, with the associated algorithm, of a suture viewable on a monitor or other visual device so that a user can see the effects of their actions, such as knot tying, as well as feel the effects with the haptic feedback device. The computer models and simulations in conjunction with the haptic surgical devices provide a more convenient and realistic teaching and training environment that can replace conventional teaching and training techniques.

BRIEF DESCRIPTION OF DRAWINGS

In order that a more precise understanding of the above recited invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which:

FIGS. 10A, 10B, and 10C are 3-dimensional computer representations of the working tip of a laparoscopic suturing device. Specifically exemplified in a simple representation is the EndoStitch™ suturing device wherein FIG. 10A shows the jaws opened and the needle affixed to the upper jaw, FIG. 10B shows the jaws closed, such as when the device is locked, or the needle position is being changed, and FIG. 10C shows the jaws open with the needle affixed to the lower jaw. Also shown in these figures is an example of a 3 dimensional representation of an object, such as a tissue or organ.

FIG. 15A is an embodiment of the pseudo code derived from the software that can be used with the subject invention.

DETAILED DISCLOSURE

Figure 1:
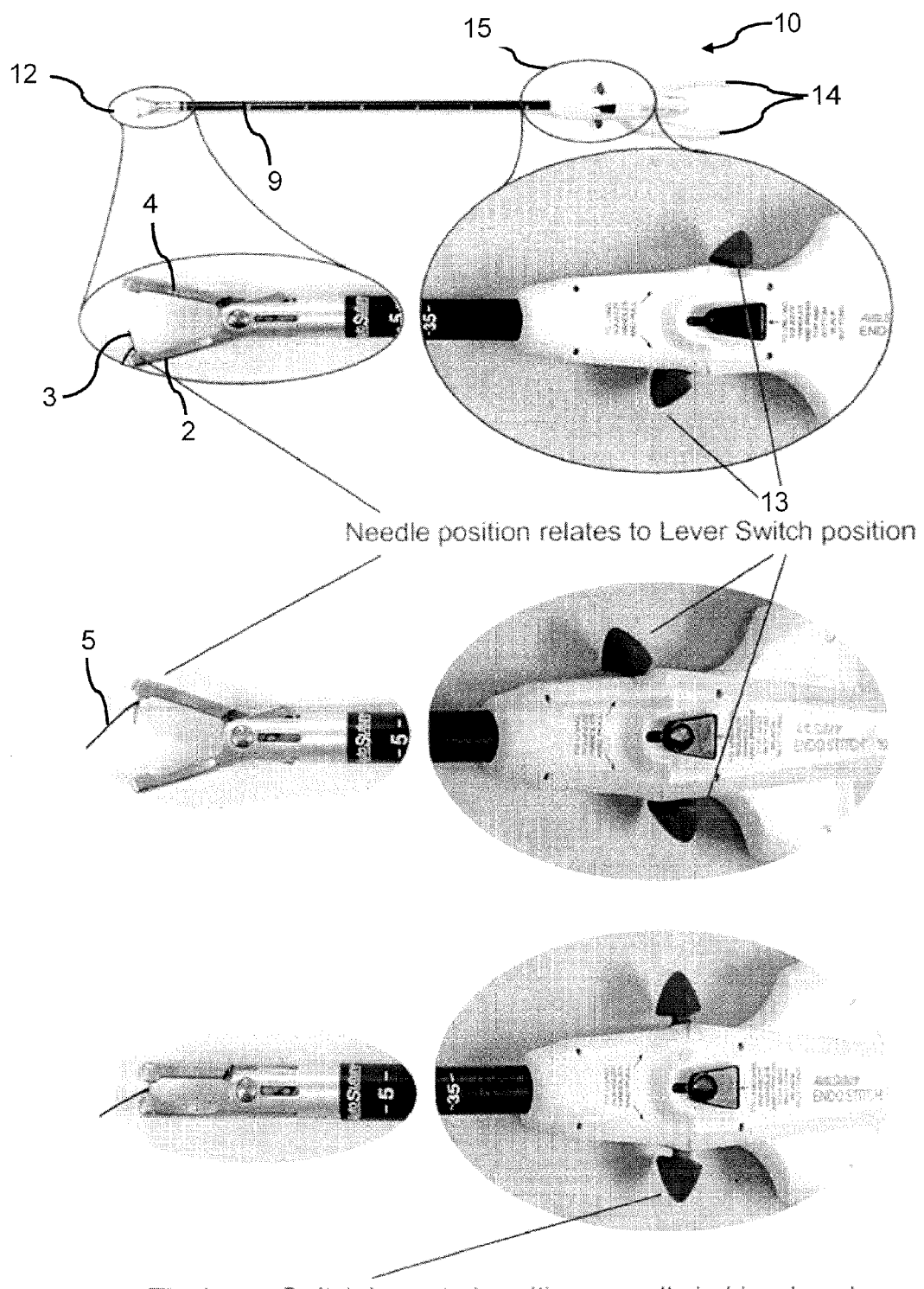
FIG. 1 is a series of photographs demonstrating the working positions of a suturing device used in laparoscopic surgeries. Shown is the EndoStitch™ suturing device with the needle positions corresponding to the lever positions on the handle.

The following description will disclose that the subject invention is particularly useful in the field of surgical procedures and, in particular, methods and devices used for training and/or teaching the use of laparoscopic surgical instruments, more particularly laparoscopic suturing instruments and even more particularly the EndoStitch™ laparoscopic suturing device. However, a person with skill in the art will be able to recognize numerous other uses that would be applicable to the devices and methods of the subject invention. While the subject application describes a use for training and/or teaching the use of laparoscopic suturing devices, other modifications apparent to a person with skill in the art and having benefit of the subject disclosure are contemplated to be within the scope of the present invention.

The terms "surgeon" or "physician" as used in the subject invention are merely for literary convenience. The terms should not be construed as limiting in any way. The devices, apparatuses, methods, techniques and/or procedures of the subject invention could be utilized by any person desiring or needing to do so and having the necessary skill and understanding of the invention.

Also, as used herein, and unless otherwise specifically stated, the terms "operable communication" and "operable connection" mean that the particular elements are connected in such a way that they cooperate to achieve their intended function or functions. The "connection" may be direct, or indirect, physical or remote.

In addition, references to "first", "second", and the like (e.g., first and second switches), as used herein, and unless otherwise specifically stated, are intended to identify a particular feature of which there are at least two. However, these references are not intended to confer any order in time, structural orientation, or sidedness (e.g., left or right) with respect to a particular feature.

The term "video display device" as used herein refers to any interactive computer or electronic device that manipulates the video display signal of a display device, such as a television, monitor, screen, or similar equipment, to display the virtual objects and virtual working tip of the subject invention. In a preferred embodiment, the video display device of the subject invention comprises any of a variety of devices capable of displaying a 3-dimensional image. In a more preferred embodiment, video display device of the subject invention is a personal computer with a monitor.

With reference to the attached figures, which show certain embodiments of the subject invention, it can be seen that the subject invention comprises a system that includes the combination of an actual instrument handle with a virtual recreation of the instrument's working tip on a video display device. In one embodiment, the system includes a haptic device with a modified input device. Particularly exemplified herein is the use of a PHANTOM Omni™ haptic device developed by SensAble Technologies, Inc. (FIG. 2) where the stylus is replaced with the modified handle from an AutoSuture™ Endostitch™ device (FIG. 1), or a handle that adequately approximates that of the Endostitch™ device.

Embodiments of the subject invention include, generally, a connection between a surgical device, such as, for example, an Endostich™ handle and the Phantom device, or other haptic device or components, the recreation of the functional or working portion of the device, such as, the working tip of the Endostich™ device, in a virtual environment, and the creation of an interactive virtual suture, for example, the application of a virtual suture to the Endostich™ needle. These and other components will be discussed in detail.

I. Operable Connection Between the Haptic Device and a Surgical Instrument

The subject invention provides methods for the modification of a surgical device or instrument for use as a computer input device. In one embodiment of the subject invention, the handle or other mechanism of manipulation of a surgical device is modified as an end effecter, so that the effects of manipulations of the surgical device are translated into signals, which can be interpreted by a computer or similar equipment. In a more preferred embodiment of the subject invention, the surgical device is modified for use with a haptic feedback device, which is operably connected to a computer that utilizes software to control the haptic feedback device. An alternative embodiment utilizes haptic components incorporated as part of the modified surgical device, such that a separate haptic feedback device is not required. In these embodiments, a user is able to interface with a surgical device and a computer to experience a virtual reality simulation of a surgical or other procedure.

Figure 2:
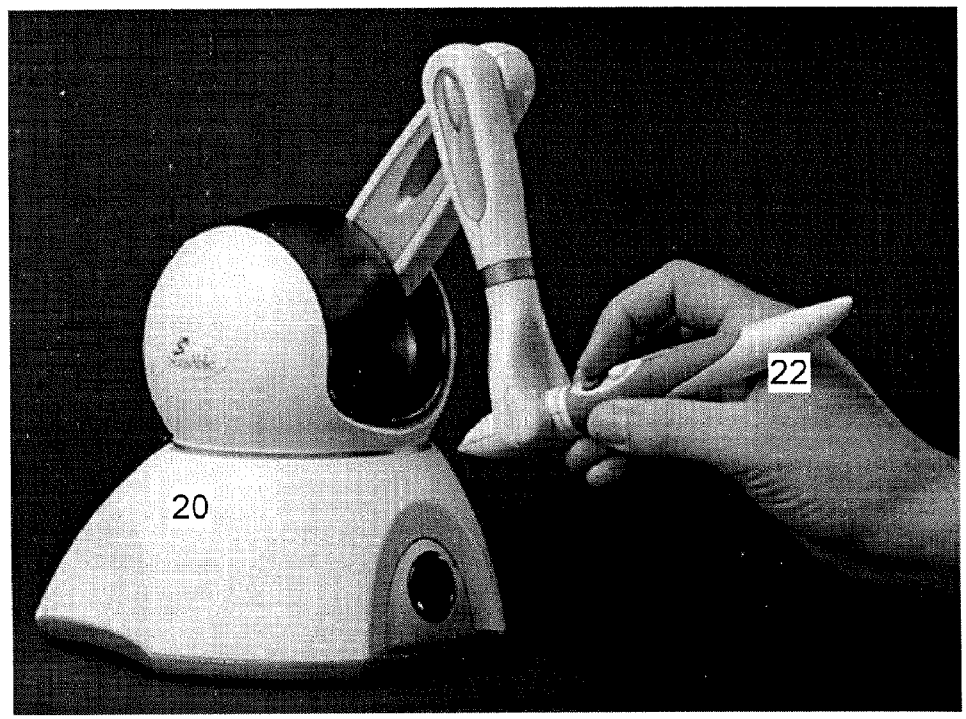
FIG. 2 is a photograph of a force feedback haptic interface device designed to convey force sensations to a user operating a device in a 3 dimensional (3D) virtual environment.

In one embodiment, a Phantom Omni Haptic Device (SensAble Technologies, Woburn, Mass.) 20 is utilized with the subject invention (FIG. 2). The Phantom Omni 20 normally utilizes a stylus 22 affixed to a stereophonic-type ¼" jack 24 (FIG. 3) as the normal mode of computer input. However, in this embodiment of the subject invention, the original user-interfacing stylus 22 is replaced with a modified handle 30 of a surgical instrument by connection to the ¼" jack 24. In a further preferred embodiment, a modified handle 30 of the Autosuture Endostich™ device is used to replace the stylus (FIG. 4). The modified handle 30 recreates the critical instrument maneuvers of: 1) positioning the jaws in open or closed stages, and 2) placing the needle in the right/left jaw, depending on the sliding lever of the device (FIG. 1).

In an embodiment of the subject invention, the modified handle 30 of the AutoSuture EndoStitch™ device is modified by utilizing any of a variety of switches and circuits, known to those with skill in the art, to translate the mechanical manipulations of the device, e.g., the squeezing of the handle and moving of the lever switches, into electrical signals. In a further preferred embodiment, one or more micro-switching circuits 40, known to those with skill in the art, are utilized to translate the mechanical manipulations into electrical signals. In a still further preferred embodiment, the micro-switches are further operably connected to a jack adaptor, known in the art, capable of receiving a stereophonic jack.

Alternative embodiments can utilize any of a variety of techniques and devices for transmitting one or more signals to the haptic device. For example, in one embodiment optical detectors such as lasers, fiber optics, or photodetectors can be utilized with the device of the subject invention.

In a still further embodiment, the handle of a surgical device can be modified to comprise haptic components within the handle. In this embodiment, the modified handle, acting as an input device, can provide input directly to a haptic device.

The operation and mechanisms of the AutoSuture EndoStitch™ device (FIG. 1) are described in detail in U.S. Pat. Nos. 5,478,344; 5,478,345; and 5,480,406. A review of these patents and the device itself reveals that in operation a specialized needle 3 is transferred between an upper jaw 4 and a lower jaw 2. The transfer of the needle 3 to and from the upper jaw 4 and lower jaw 2 is accomplished with a series of bars and blades, within an elongated housing, whose motions are controlled by squeezing the handle arms 14 and changing the position of a lever switch 13. FIG. 1 illustrates how the position of the lever switch 13 correlates to the position of the needle 3.

Therefore, in a specific embodiment of the subject invention, shown for example in FIGS. 5, 6, 7 and 8, the elongated housing 9 and the various bars and blades contained therein for controlling the needle 3 are disconnected from the handle housing 32 leaving the lever switch 13 in place. In addition, the spring-biased center rod 7 is truncated just before the lever switch 13, and the cut end covered with a non-conductive tip 8, to maintain the integrity and working mechanisms of the handle arms 14. The removal of the elongated housing 9 can provide access to the internal mechanisms within the handle of the device. Thus, in one embodiment, the handle can be further adapted to receive the ¼" jack.

It next becomes necessary to translate the motions of the lever switch 13 and the squeezing of the handle arms 14 into one or more signals that can be sent to and interpreted by software stored on a computer readable medium accessible by a computer. Therefore, in a preferred embodiment, one or more electrical microswitches are fixedly positioned in or on the handle housing 32 such that the motions of the lever switch 13 trigger the one or more microswitches 40. In a more preferred embodiment, at least two microswitches 40 are utilized with the lever switch 13 (FIG. 6), such that motion of the lever switch 13 will trigger either the upper jaw microswitch 41 position or the lower jaw microswitch 42 and translate the motion to a computer model.

In a standard EndoStitch™ device, the motion of the spring-biased center rod 7 is initiated by squeezing the handle arms 14, which actuate the center rod 7 to move towards the working tip 12 of the device. These motions can also be translated into an electronic signal in the modified handle device 30 by the use of one or more microswitches. Thus, in one embodiment, at least one center rod microswitch 43 is positioned in or on the handle housing 32 such that the motion of the truncated spring-biased center rod 7, caused by squeezing the handle arms 14, triggers the center rod microswitch 43, translating the motion to an electrical signal for computer simulation of the effect caused by the handle manipulations.

The transmission of the various microswitch signals from the modified EndoStitch™ device to the Phantom Omni device can be accomplished by a variety of methods and devices known to those with skill in the art. For example, the switches can be hardwired to the Phantom Omni device for permanently affixing the modified EndoStitch™, or other end effector device. Alternatively, any of a variety of connectors and jacks can be used to operably connect the modified handle to the Phantom Omni device.

Figure 3:
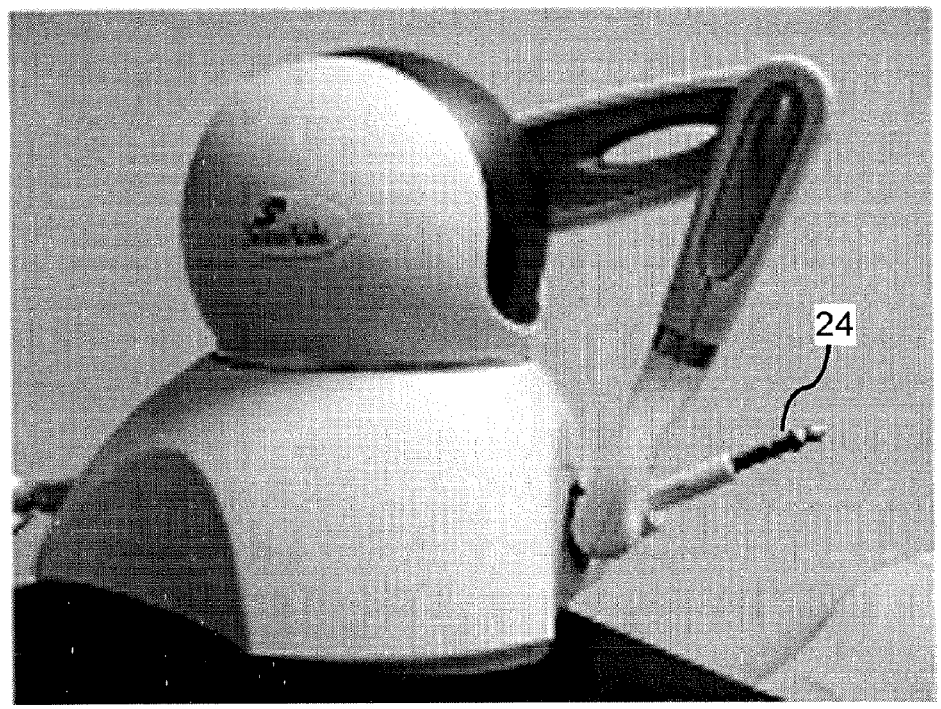
FIG. 3 is a photograph of the haptic interface device of FIG. 2 with the stylus cover removed to expose the stereophonic connector.
Figure 4:
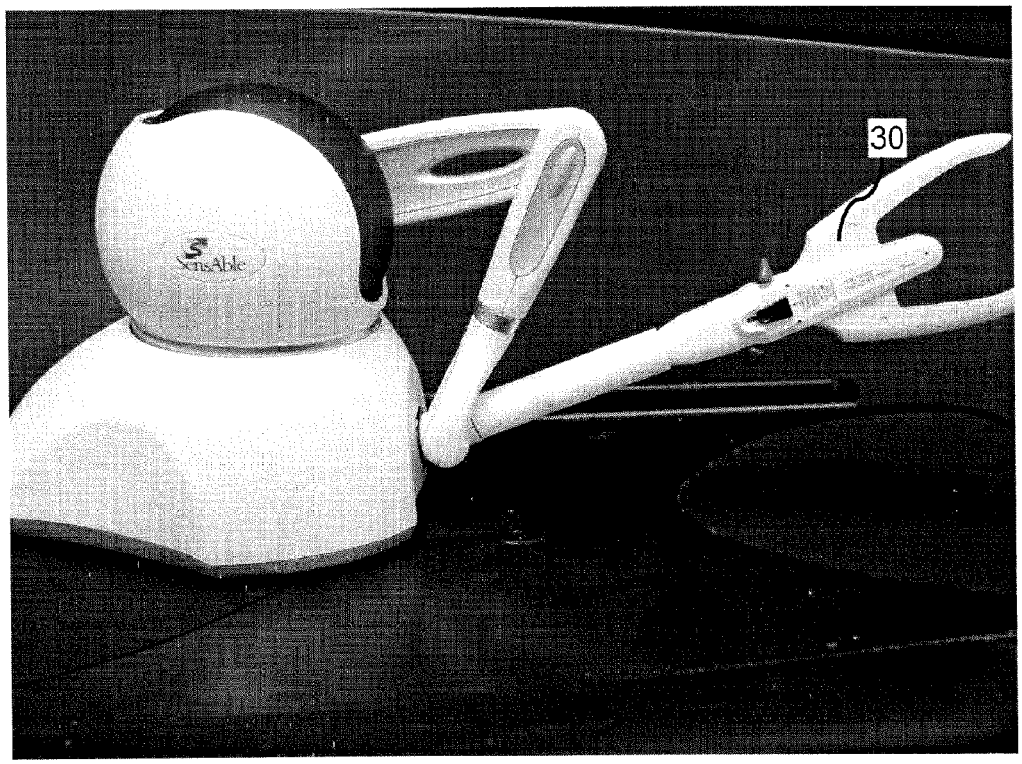
FIG. 4 is a photograph of the haptic interface device of FIG. 3 with the stereophonic connector engaged with an embodiment of the laparoscopic suturing device of the subject invention.

As can be seen in FIGS. 2 and 3, the Phantom Omni device 20 stylus 22 can be removed to expose a ¼" stereophonic jack plug 24. To connect the modified EndoStitch™ handle 30 to the Phantom Omni device 20 usually requires forming an operable connection to the ¼" stereophonic jack plug 24 of the Phantom Omni device. While many techniques or methods can be employed to make such a connection, the Phantom Omni device is designed with a ¼" jack plug to facilitate such attachments.

Figure 5:
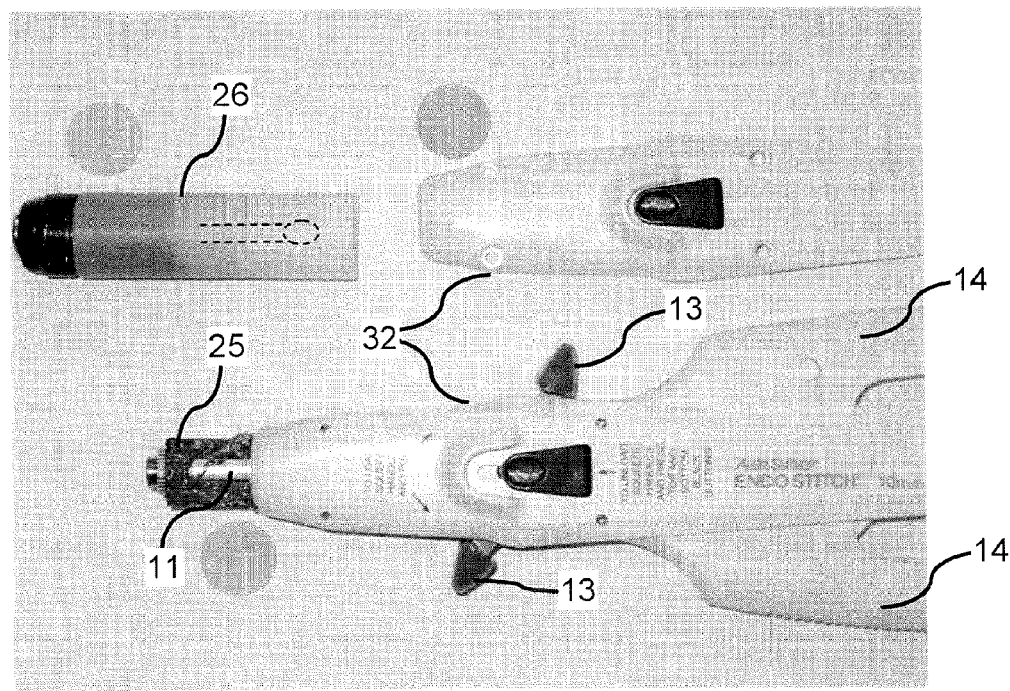
FIG. 5 is a photograph of an embodiment of a modified laparoscopic suturing device of the subject invention that can be connected to a haptic interface device, for example, via the stereophonic connector. Shown are: 1. stereophonic jack adaptor; 2. back cover of the laparoscopic suturing device; 3. original handle of the laparoscopic suturing device modified with a standard electrical jack connected to multiple microswitches.
Figure 6:
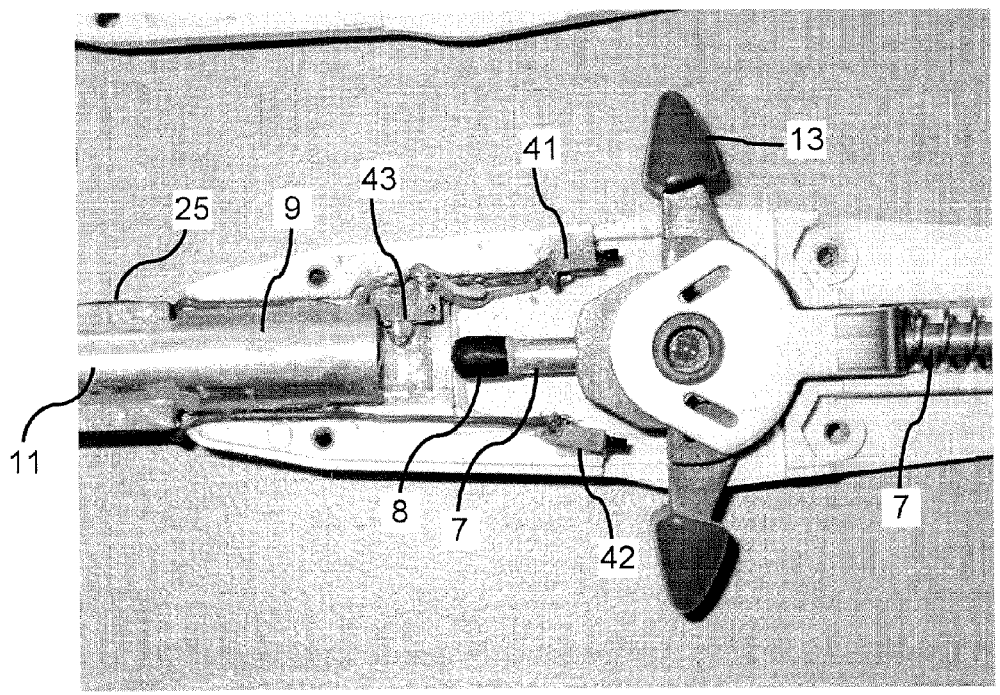
FIG. 6 is a photograph of the internal components of an embodiment of a modified haptic interfacing laparoscopic suturing device of the subject invention. In this embodiment, microswitches are utilized to translate the manipulations of the lever switch and handle levers into electrical signals that are interpreted by the haptic interface device and converted with appropriate software into a 3-dimensional virtual representation of the effects of the manipulations on the working tip of the device.
Figure 7:
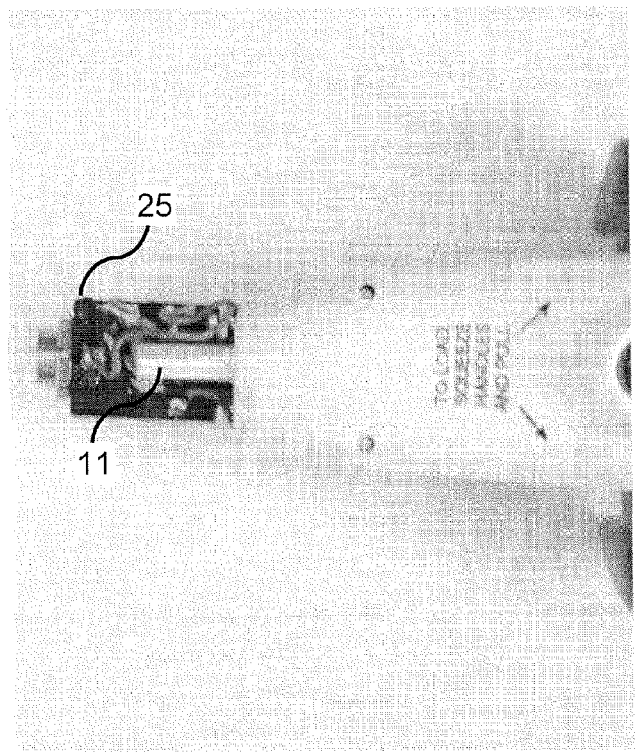
FIG. 7 is a photograph of an electrical connector, such as a jack adaptor, utilized with an embodiment of the subject invention to engage the handle of the suturing device with the haptic interface device.
Figure 8:
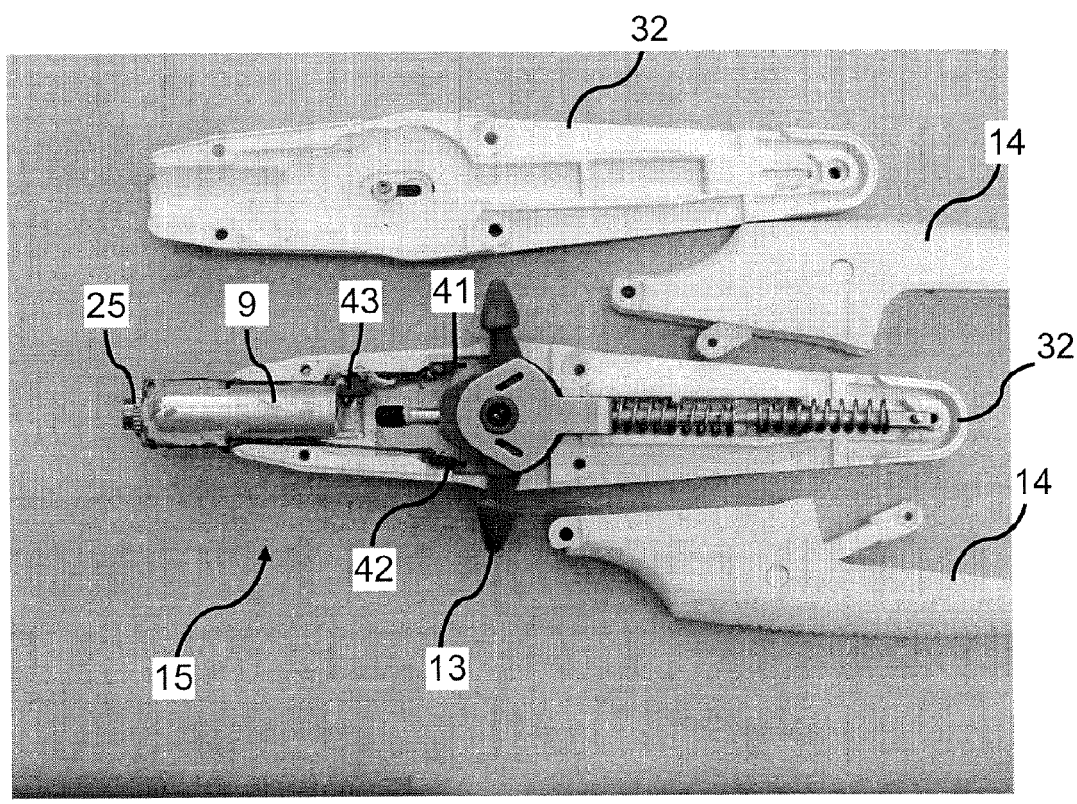
FIG. 8 is a photograph of the disassembled handle end of an embodiment of the haptic interfacing laparoscopic suturing device of the subject invention.

Thus, in a preferred embodiment, the one or more microswitches are operably connected to a jack connector 25, for example, as shown in FIGS. 5 and 7. Any of a variety of jack connectors known in the art could be utilized with the subject invention. A person with skill in the art would be able to determine the appropriate type and size of jack connector necessary to establish connection with the ¼" jack plug of the Phantom Omni device 20. For example, in one embodiment a standard phone jack connector could be utilized to more adequately fit the dimensions of the EndoStitch™ handle. In this embodiment, a housing replacement rod 9 having one or more flanges 11, for example, as shown in FIGS. 6 and 7, can be used to support a jack connector. Thus, the ¼" jack plug 24 of the Phantom Omni device 20 can be inserted directly into the jack plug 25 affixed to the handle of the modified EndoStitch™ handle. Alternatively, if the jack connector is not compatible with the ¼" jack plug, a jack plug adaptor 26 could be used between the modified EndoStitch™ handle 30 and the Phantom Omni ¼" jack plug 24. Jack adaptors 26 are well known in the art and are utilized to connect numerous types and sizes of jack connectors. If required, a person with skill in the art would be able to determine the type and size of jack adaptor 26 necessary for use with the embodiments of the subject invention.

Figure 9A:
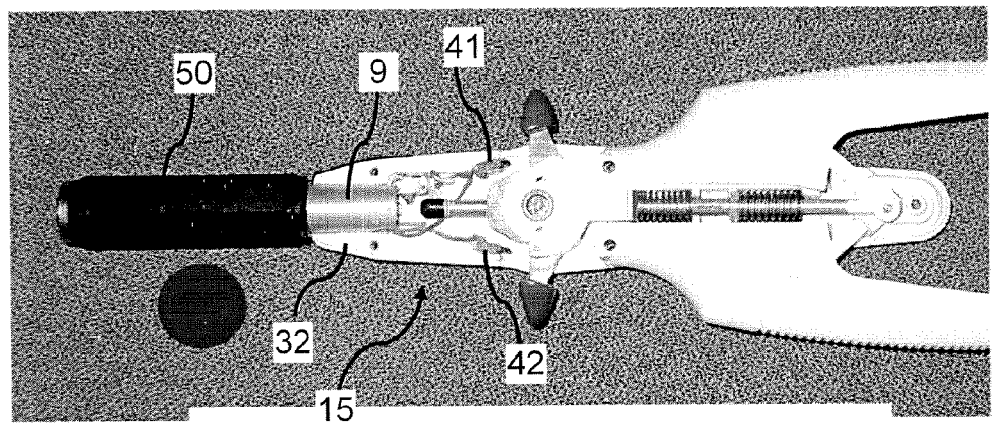
FIGS. 9A and 9B illustrate an embodiment of the subject invention utilizing a cable extension device fixedly attached to the handle of the laparoscopic suturing device of the subject invention.
Figure 9B:
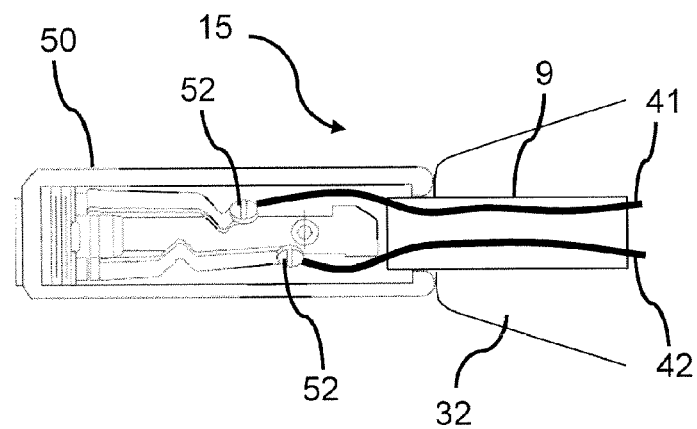

In a further alternative embodiment, the EndoStitch™ handle can be modified, as described above, but utilizing a more permanent adaptor. For example, FIGS. 9A and 9B illustrate an example of an EndoStitch™ device modified with a cable extension jack 50. The wiring of the switches 41 and 42 is conducted through the replacement rod 9, as shown, for example, in FIG. 9B, and connected to the terminals 52 within the cable extension jack 50. The cable extension jack can be permanently affixed to the EndoStitch™ handle by any means known in the art. This embodiment provides a more stable connection to the Omni Haptic Device.

In an alternative embodiment, the haptic elements of the system can be incorporated with the handle of a modified AutoSuture™ EndoStitch™ device, or a handle that adequately approximates that of the AutoSuture™ EndoStitch™ device. In this embodiment, the modified handle can be operably connected to the video display device. The video display device can utilize software that, when executed, provides information to the modified handle that causes a haptic response to be transmitted to the handle. In a still further alternative embodiment, the information transmitted to the modified handle and the haptic response thereto coincides with the 3-D display of the working tip of the device on the video display device. Thus, in this embodiment, manipulations of the handle can transmit information to the video display device that causes a modification of the display of the device's working tip thereon. The video display device can also transmit information to the modified handle pertaining to the display of the working tip, or changes thereto. The information transmitted to the modified handle causes a haptic response that coincides with the display of the working tip on the video display device.

II. Software Interface for Modeling Virtual Environment

Figure 13:
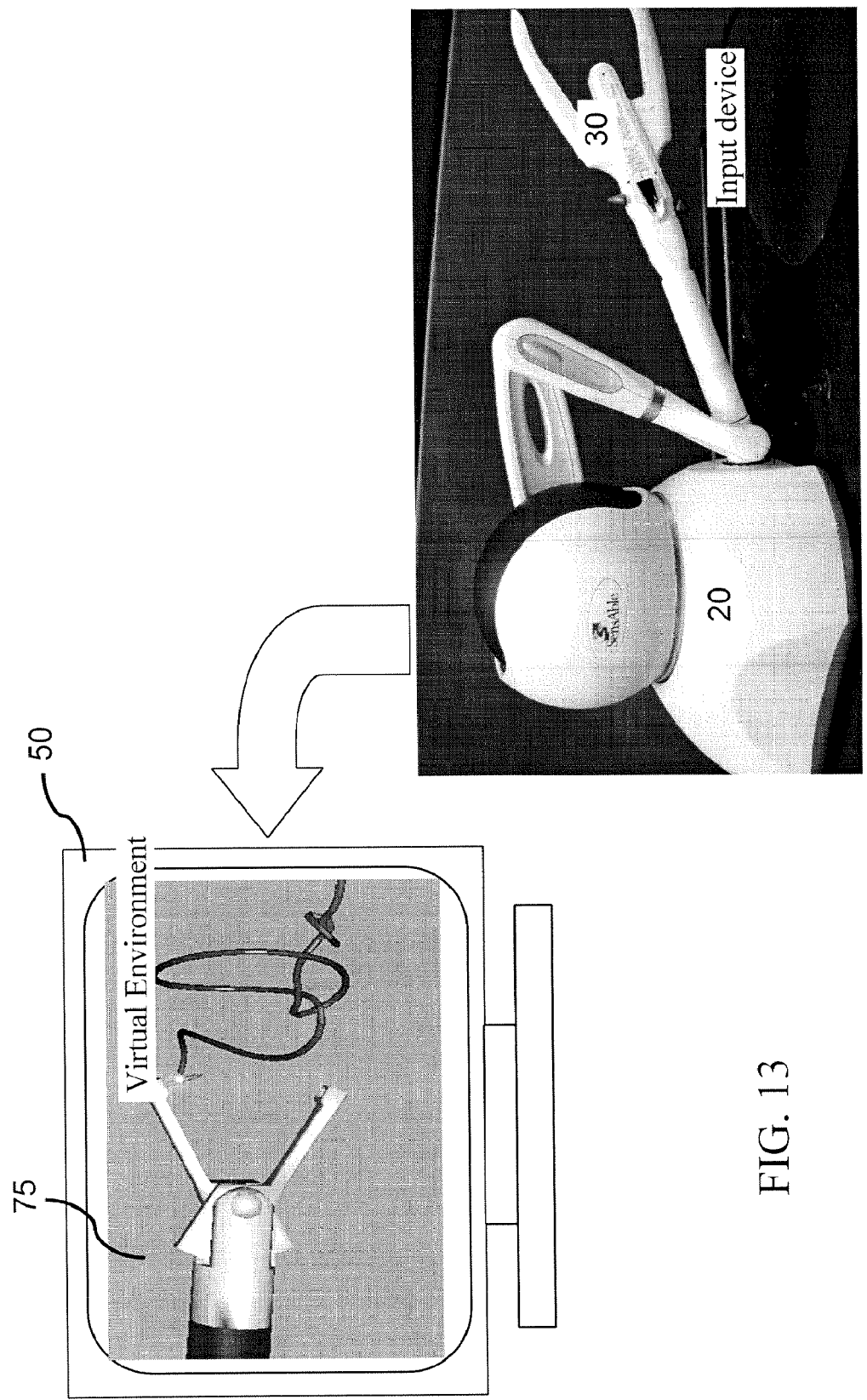
FIG. 13 illustrates how the haptic interfacing suturing device of the subject invention can be used to simulate the feel of the actual motions and actions required during a laparoscopic suturing technique and display in real-time the results of those motions and actions in a virtual environment on a virtual suture or other virtual object.

During minimally invasive procedures, a surgeon will usually see the in vivo working tip of the device being used within the laparoscopic field of vision. Therefore, to accurately simulate a surgical environment for training, the trainee surgeon must be able to see a version of the working tip normally controlled by the device handle being manipulated. As described above, in the subject invention, the handle manipulations of a device can be converted into at least one electrical signal that can further be transmitted to a computer or other device capable of interpreting the signal(s). A computer, or other signal interpreting device, can be programmed or otherwise designed to interpret the signal(s) from the modified device handle and present a 3-dimensional visual representation, or 3-dimensional (3-D) virtual image 75, of the manual manipulations that caused such signal(s). (FIG. 13)

There are a numerous software packages and programming languages that can be used to recreate or model a 3-D virtual image 75 of a device's working tip, interpret the electrical signals generated by a modified device, and change the modeled image display to correspond to the manipulations of the modified device. In preferred embodiments, the electrical signals generated by a modified device, such as the modified EndoStitch™ handle 15 are used by a computer having software capable of altering a modeled virtual image 75 of the working tip displayed on a monitor 50 or similar visual aid. It is known in the art to utilize such techniques to model a "virtual environment" in which a surgeon can see a 3-D image that simulates a real environment and/or a device's working tip wherein the surgeon's manipulations of a modified device handle, such as the modified EndoStitch™ device handle, cause an immediate or almost immediate effect on the virtual image. A number of state-of-the-art technologies: advanced graphics, both hardware and software (novel surface representations, real time recording of hand motion in virtual scene, etc.) can be used to simulate devices and/or create a variety of virtual environments.

Figure 11B:
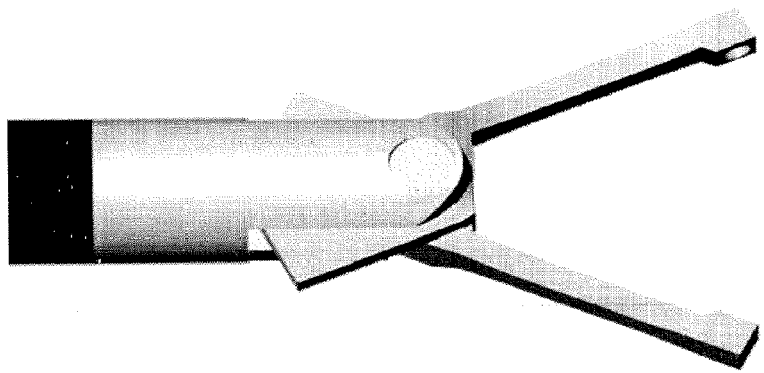
FIGS. 11A and 11B are embodiments of 3-dimensional computer representations of the working tip mesh model (12A) and the rendered model of an Endostich™ working tip (12B) of the subject invention.
Figure 11A:
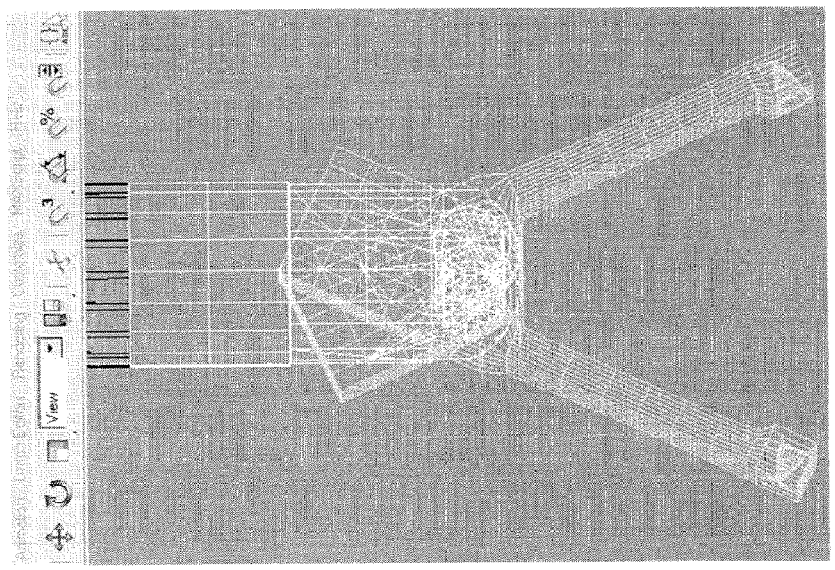

In one embodiment of the subject invention, a 3-D virtual environment or a scene is created or modeled that simulates, for example, an intracorporeal or in vivo environment that a surgeon is likely to encounter and images of the working device tip are imported into the virtual scene. (FIG. 13). In a specific embodiment, 3-D virtual images of the open and closed jaws of the EndoStitch™ device's 10 working tip 12 can be recreated using the Autodesk® 3ds Max® 8 software package. Once created, the images of the open and closed jaws can then be imported into a virtual scene. FIGS. 10A-10C illustrate an example virtual environment wherein various images of the virtual open and closed jaws of the EndoStitch™ device's working tip have been imported. FIG. 11A presents the underlying triangular mesh of a more detailed version of the EndoStitch™ device's working tips and FIG. 11B shows an example of the rendered model of the instrument's working tip 12.

Figure 12A:
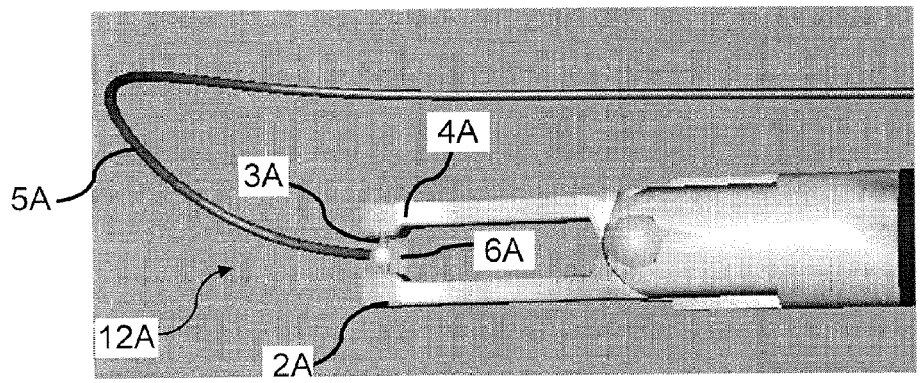
FIGS. 12A-12E are 3-dimensional computer representations of the working tip of a laparoscopic suturing device. Specifically exemplified in this series of representations is the EndoStitch™ suturing device interacting in a virtual environment with a realistic "virtual" suture, created by the software of the subject invention, to tie a typical surgeons half-hitch suture.
Figure 12B:
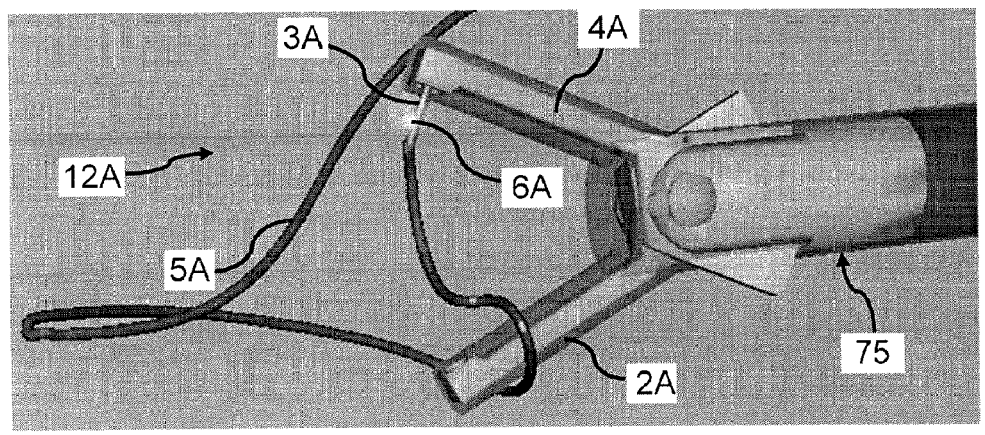
Figure 12C:
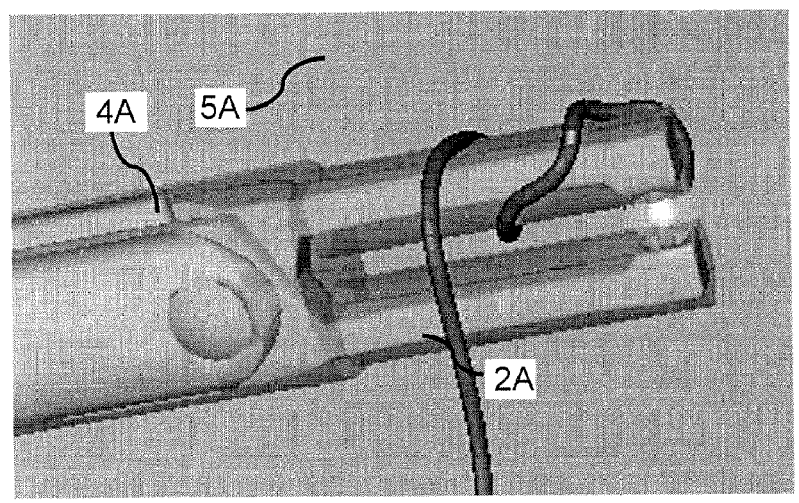
Figure 12D:
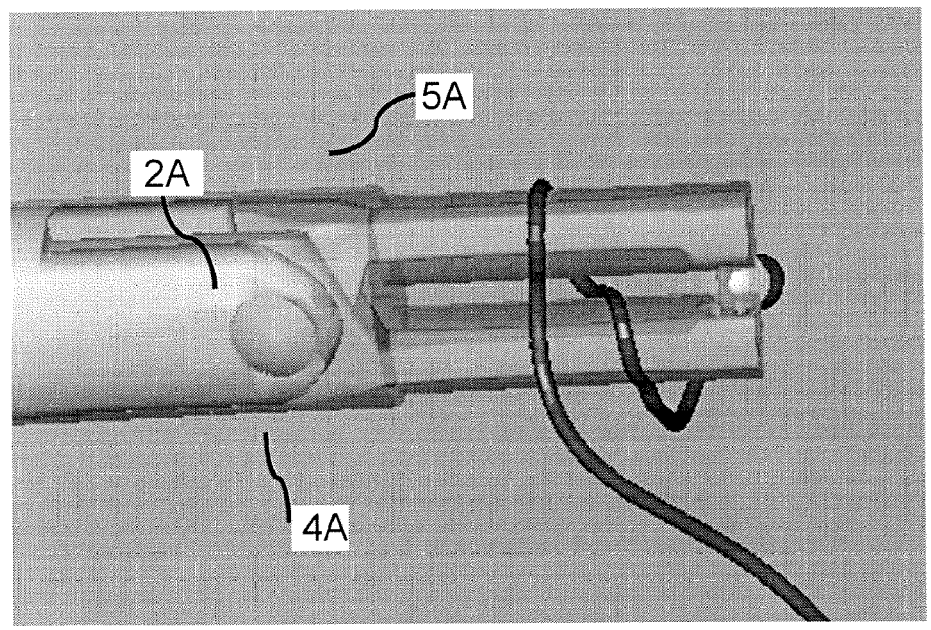
Figure 12E:
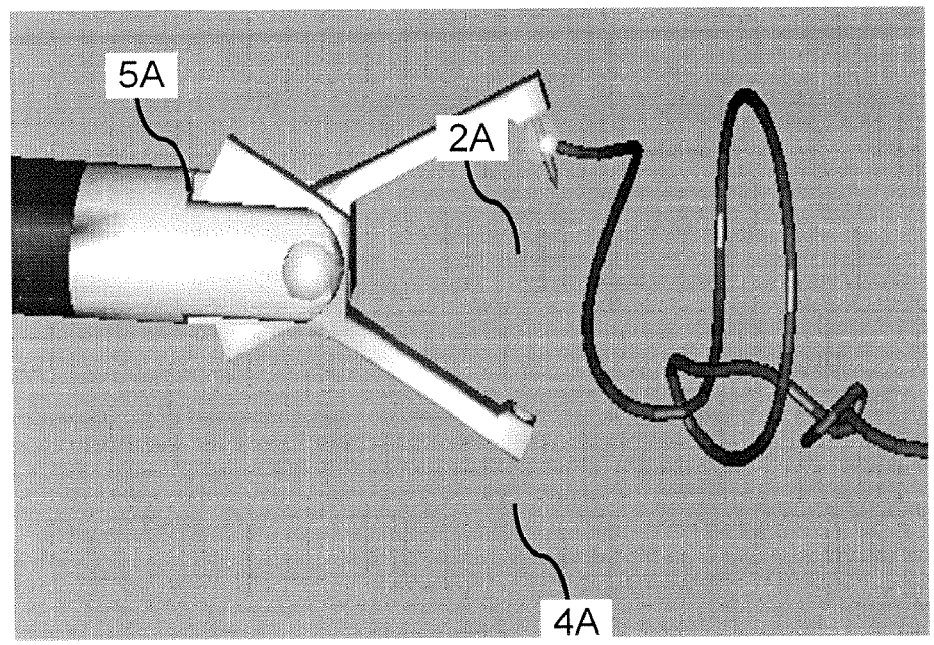
Figure 14A:
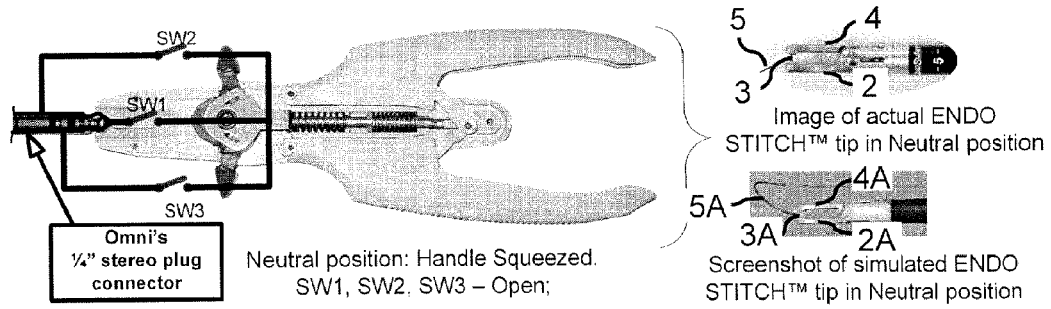
FIG. 14A-14D show switching diagrams for an embodiment of the subject invention utilizing an Endostich™ device handle. By squeezing the handle and manipulating the lever switch thereon, the position of upper and lower jaws of the Endostich™ device can be changed for each step of the suturing process and knot tying. In the subject invention, electrical components, such as for example, microswitches are utilized to translate these mechanical motions into electrical signals, as indicated by the switching diagrams overlaying the handle device, that are used to generate identical movements in a virtual environment.
Figure 14B:
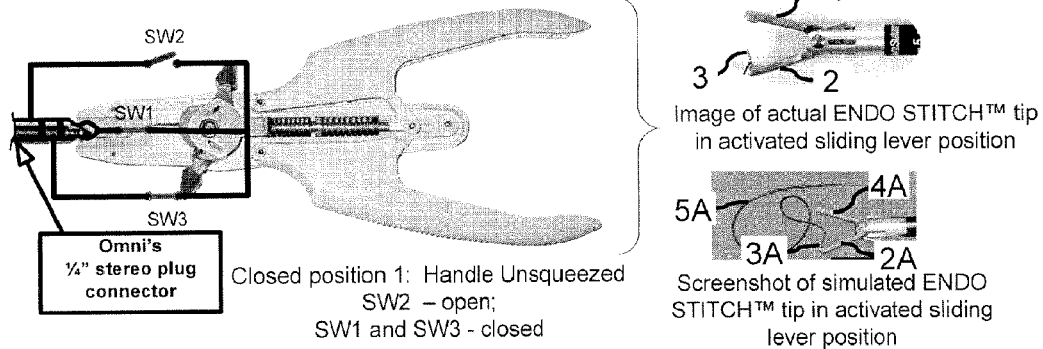
Figure 14C:
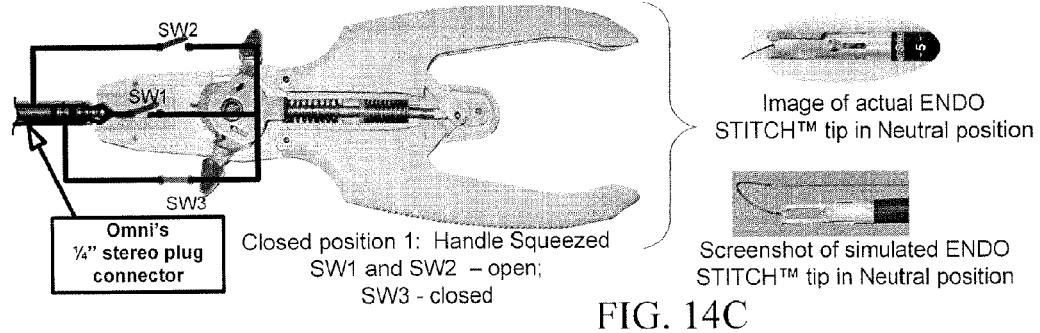
Figure 14D:
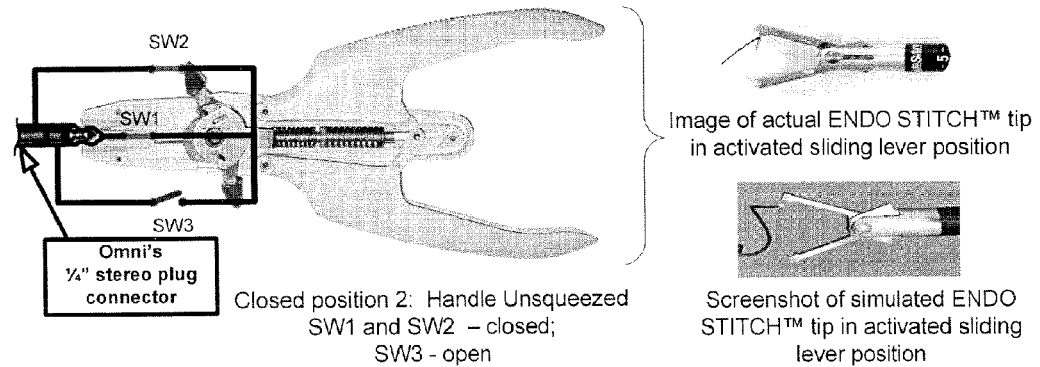
Figure 15B:
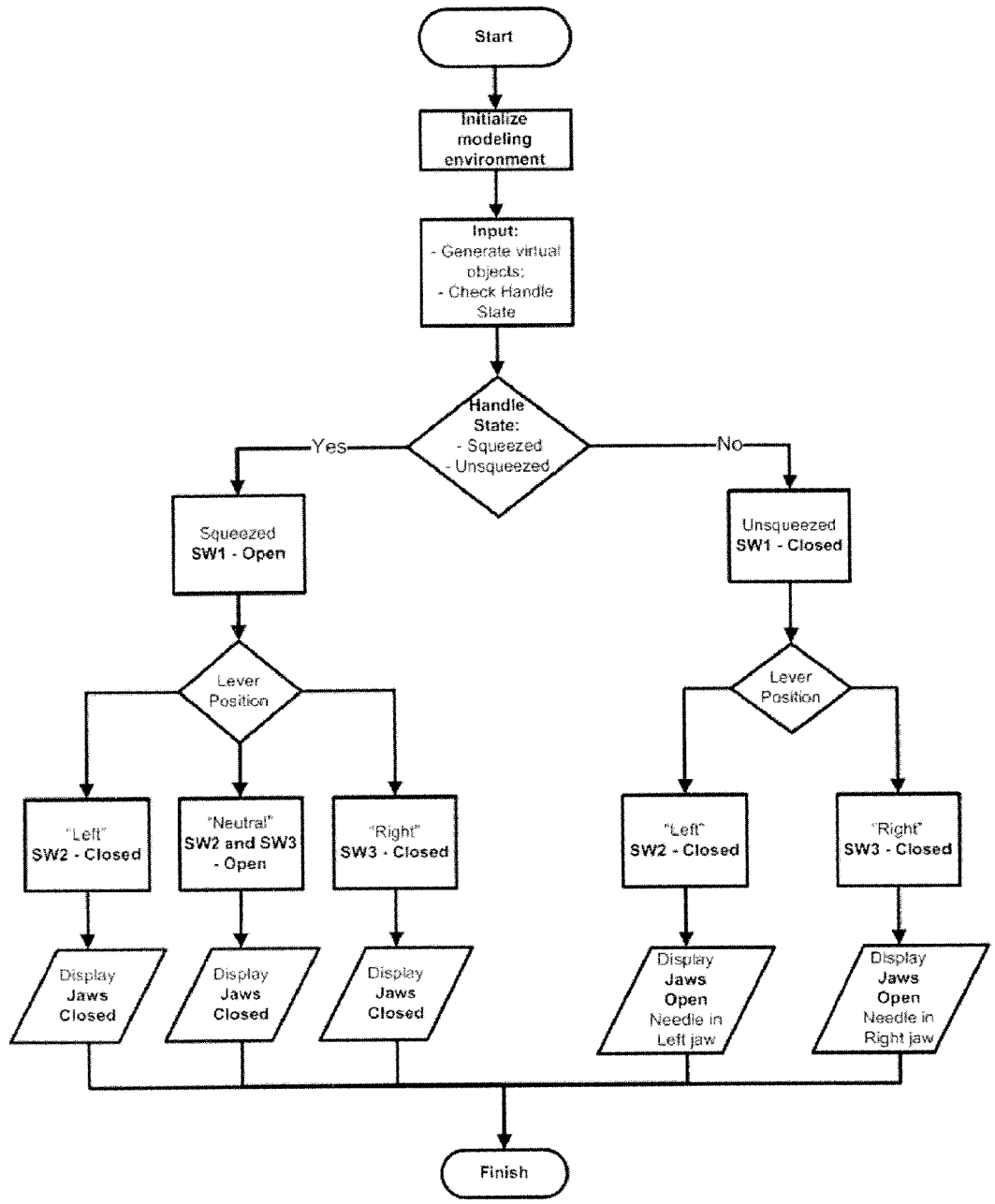
FIG. 15B is an embodiment of an algorithm derived from the pseudo code of FIG. 14A.

With regard to FIGS. 14A-14D, it can be seen that, in an embodiment utilizing the EndoStitch™ device, by squeezing the handle arms and changing the position of the lever switch 13 causes the opening and closing of the various switches installed in the modified handle of the device. The opening and closing of the switches, or the combination thereof, provides information to a computer that displays on its monitor a modeled virtual working tip 12A comprising the upper jaw 4A and the lower jaw 2A. The information provided to the computer determines whether the computer displays the 3-D virtual jaws in an open (for example, FIGS. 10A and 12B), closed (or neutral) (for example FIGS. 10C and 12A) position, and the position of the virtual needle 3A of the device. For example, FIG. 14A shows that with the handle arms 14 squeezed and the lever switch 13 in a neutral position, the virtual upper jaw 4A and the virtual lower jaw 2A of the virtual image 75 are closed. By rotating one or the other side of the lever switch 13 forward, the virtual needle 3A and the associated virtual suture 5A can be moved from either the virtual upper jaw 4A or the virtual lower jaw 2A. The ability to move the virtual needle 3A, combined with specific movements enables a surgeon to tie knots or create other stitches in a virtual endoscopic environment with the subject device. FIG. 15A is an outline of one embodiment of the pseudo-code that can be used by the subject invention. FIG. 15B is an embodiment of the algorithm used to control the operation of the upper jaw microswitch 41, the lower jaw microswitch 42, and the center rod microswitch 43 and their effect on the virtual display image 75 of the EndoStitch™ device 10.

In a further embodiment, the above mentioned software package is utilized on a Pentium IV 3 GHz with 1 GB of RAM computer equipped nVidia GeForce 6800 video card. However, it should be understood, that a person with skill in the art would be able to devise any of a variety of hardware devices and combinations thereof suitable for use with the subject invention. In preferred embodiments, the hardware will have adequate memory, speed, and display capabilities to accurately simulate a virtual environment and a device working tip, and be capable of providing appropriate haptic and visual feedback to accurately simulate a surgical procedure as it would be performed with the EndoStitch™ device, or other surgical instrument utilized with the subject invention.

In a preferred embodiment, the software package of the subject invention is based on open source OpenGL graphic libraries, standard C++ programming language, and includes libraries from Academic developer version of OpenHaptics™ toolkit (SensAble Technologies, Inc.). The package was developed to support the real time manipulations of the needle and suture, which accompany the modeled instrument in the virtual environment. FIG. 13 is an example of a complete system of the subject invention including the Phantom Omni haptic device modified with the handle of the AutoSuture EndoStitch™ device and a computer monitor 50 showing a virtual image 75 of the working tip 12A of the device.

III. Application of a Suture to a Virtual EndoStitch™ Device Needle

In a preferred embodiment of the subject invention, the AutoSuture EndoStitch™ device (US Surgical/Tyco) 10 is modified to function with the Phantom® Desktop™ Haptic Device (SensAble Technologies, Woburn, Mass.) 20. The AutoSuture EndoStitch™ device is for single-patient use and specially designed for use in endoscopic surgeries to create interrupted or running stitches in tissues. The device comprises two jaws, an upper jaw 4 and a lower jaw 2, that are controlled by a squeezable handle 14 and lever switch 13. A specialized needle 3 having a pre-loaded suture 5 is positioned between the upper jaw 4 and the lower jaw 2 and passed therebetween such that with specific movements and by utilizing the handle mechanisms to move the needle from one jaw to the other, various sutures and knots can be tied during an endoscopic surgical procedure.

Therefore, to accurately simulate in a virtual environment a surgical procedure using the AutoSuture EndoStitch™ device, it is necessary to also develop model of a "virtual suture" 5A that can accurately visually depict the motions and reactions that would be encountered during a surgical procedure. Development of a proper model for a suture has been a challenge for surgical virtual reality. While there are many algorithms in the prior art, they often present some limitations and are generally not available for common shareware.

The subject invention utilizes a suture simulation program that provides a "virtual suture" capable of interacting, within a virtual environment, with the virtual working tip 12A of an EndoStitch™ device. FIGS. 12A-12E show an image series of virtual motions for tying a typical half-hitch knot utilizing the simulation program of the subject invention. In a preferred embodiment of the subject invention, the simulation program is based on a Follow-The-Leader (FTL) algorithm, known to those with skill in the art, wherein the virtual suture thread 5A is modeled as a mass-point system with connectivity links having a fixed length. In this embodiment, a first mass point is connected to a second mass point by a designated connectivity link, the second mass point is connected to a third mass point by a designated connectivity link, and so on. In this embodiment, the model considers only translation and does not include rotational factors for each point or for the link connecting to its two nearest neighbor points. However, in an alternative embodiment, such rotational factors can be included in the programming.

In a virtual environment, the software enables each mass point that makes up a virtual suture to be grabbed and moved by a virtual surgical working tip 12. If point $p_n$ is moved, then its neighbors, and $p_{n-1}$ and $p_{n+1}$, will follow in order to maintain the fixed length of the links. These movements will cause the next neighbors, $p_{n-2}$ and $p_{n+2}$, to follow and so on until all necessary neighbors have been moved. An example of this algorithm is illustrated in FIG. 15. When modeling the EndoStitch™ device, the first mass point 6A of a suture thread 5A is considered to be one attached to the virtual suture needle 3A so that the user can manipulate the virtual suture 5A by moving the virtual needle 3A attached to the virtual instrument working tip 12A.

Figure 16:
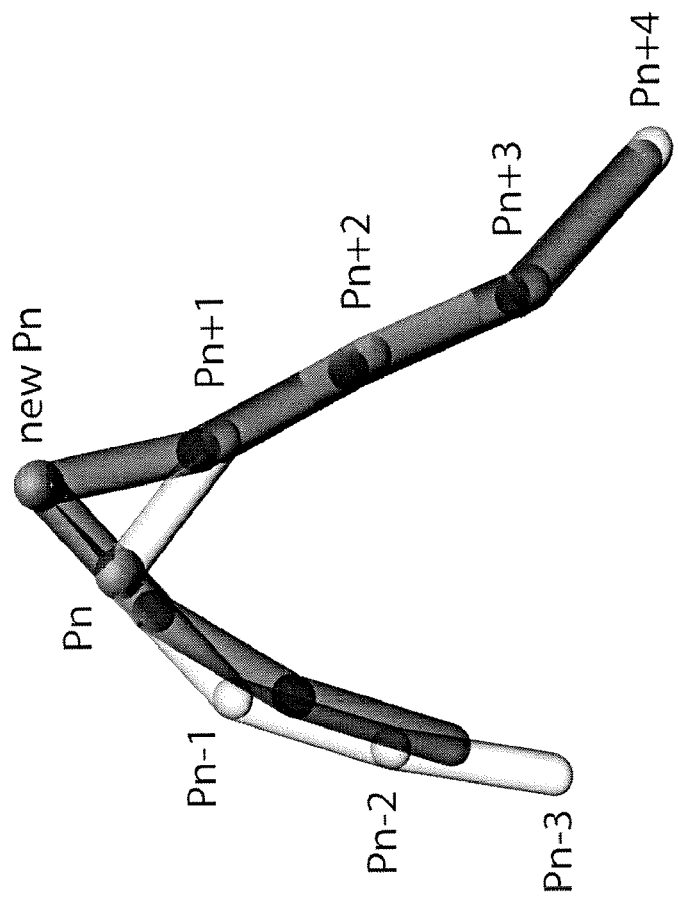
FIG. 16 is a graphical illustration of the algorithm for generating the suture model utilized with an embodiment of the subject invention. In this embodiment, the first mass point, $p_n$, is attached to the needle such that the suture can be manipulated by moving the computer modeled needle attached to the instrument tip. Thus, when $p_n$ is moved, mass points $P_{n-1}$, $P_{n+1}$, follow, then $P_{n-2}$, $P_{n+2}$, then $P_{n-3}$, $P_{n+3}$, etc.
Figure 17:
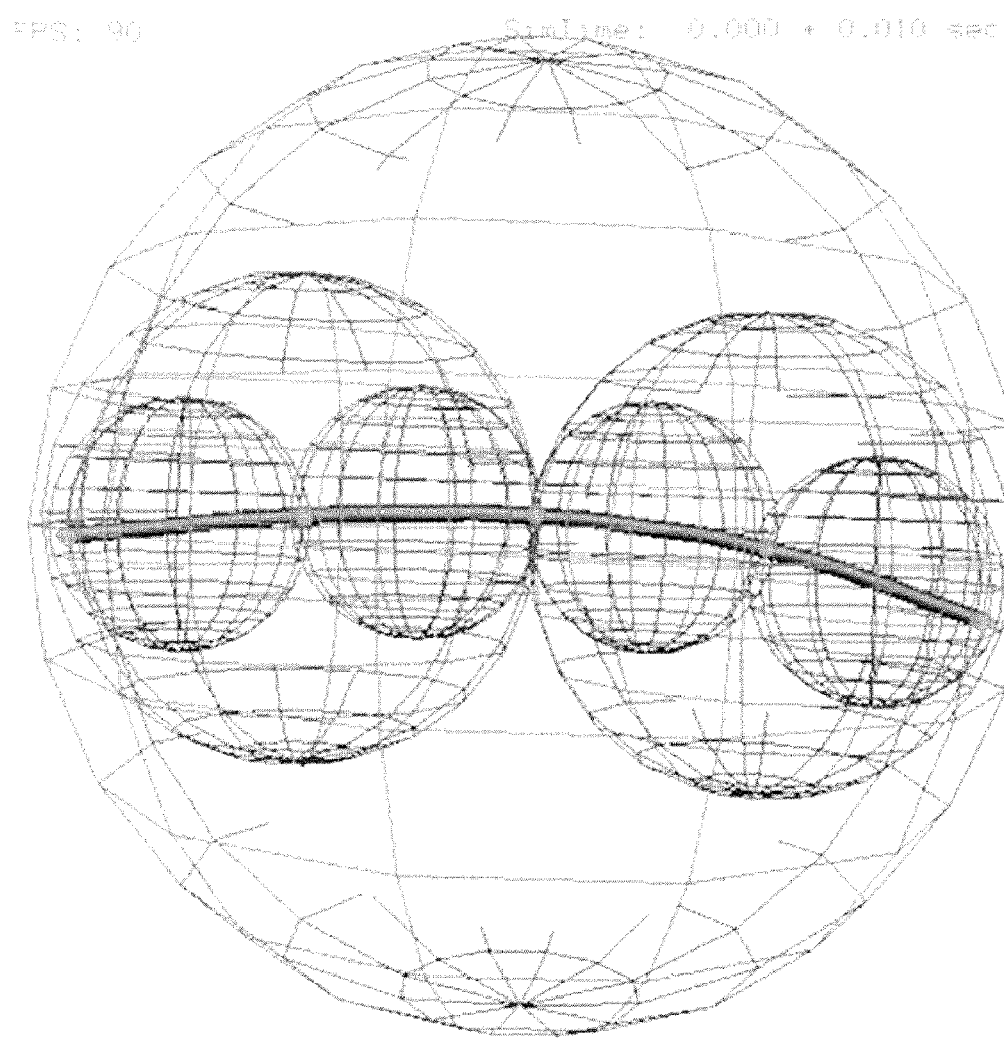
FIG. 17 is an illustration of Sphere Bounding Volumes (SBV) bounded around 4-link thread for collision detection during manipulation of virtual thread.

In addition, to more accurately model a virtual suture thread, it also necessary to simulate the suture's interaction with other objects in the virtual environment, including the virtual working tip 12A of the device. This can be accomplished by any of a variety of programming techniques known to one with skill in the art. In a preferred embodiment of the subject invention, collision detection is performed based on a Bounding Spheres technique, as known in the art, and shown, for example, in FIG. 16.

The devices and methods of the subject invention can have innumerable uses for training that permit the repeated performance of maneuvers that accurately simulate an existing or new surgical instrument, or other device, but in a virtual world. The device of the subject invention can also be used to test and refine new devices in the virtual environment before they used in a real environment, surgical or otherwise. Alternative embodiments can also create simulations wherein the motion paths in 3-dimensional space of an experienced surgeon or educator can be recorded and used to later guide a trainee in a virtual environment, allowing the trainee to be guided by the recorded educator's path.

A further alternative embodiment can utilize certain devices and methods of the subject invention to perform procedures at long distance. For example, the modified surgical handle combined with a haptic feedback device can be used to guide an actual instrument's working tip mounted, for example, on a movable arm capable of 3-dimensional motion. A surgeon in the next room or across country could utilize the actual device handle to send signals to an actual device tip that has been pre-positioned for an endoscopic surgical procedure. This could permit a specialist in one location to perform surgical procedures around the world.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A system for creating an interactive virtual model of a surgical instrument within a virtual environment, the system comprising:
    an input device that is manipulated similarly or identically to the handle of the surgical instrument, such that the manipulations used with the input device are similar or identical to one or more maneuvers used to operate one or more controls of the surgical instrument working tip and where the input device manipulations generate at least one signal that corresponds to one or more of the maneuvers that are made with the handle of the surgical instrument;
    at least one haptic feedback device in operable connection with the input device, such that the at least one signal is transmitted to the at least one haptic feedback device and wherein the haptic feedback device transmits haptic feedback information, including information pertaining to the at least one signal, to the input device;
    a display device in operable connection with the at least one haptic feedback device wherein information from the at least one haptic feedback device is transmitted to the display device; and,
    a computer application stored on a computer readable medium accessible by display device that, when executed,
        generates a virtual model in the virtual environment of the surgical instrument working tip on the display device, such that the virtual model of the working tip is similar or identical to that of the surgical instrument and is controlled by manipulation of the input device;
        interprets the information received from the at least one haptic feedback device;
        modifies at least one of a representation and orientation of the virtual model of the working tip of the surgical instrument on the display device in response to information from the haptic feedback device; and
        transmits information back to the haptic feedback device that causes a haptic response corresponding to the modified virtual model display to be transmitted to and detectable with the input device,
    such that the manipulations of the input device correspond to one or more control maneuvers used with a surgical instrument and cause modification of the display of the virtual model of the working tip of the surgical instrument.

2. The system, according to claim 1, wherein the input device operates similarly or identically to a handle of a laparoscopic suturing instrument.

3. The system, according to claim 2, wherein the input device operates similarly or identically to a handle of an AutoSuture® EndoStitch™ laparoscopic suturing instrument.

4. The system, according to claim 3, wherein the working tip displayed in the virtual environment on the display device resembles that of an AutoSuture® EndoStitch™ laparoscopic suturing instrument.

5. The system, according to claim 1, wherein the display device is a computer monitor.

6. The system, according to claim 1, wherein the haptic feedback device is a Phantom® Omni™ (SensAble Technologies) haptic device.

7. A system for creating an interactive virtual model of a surgical instrument within a virtual environment, the system comprising:
    an input device comprising at least a handle from a surgical instrument, where the handle is modified to generate at least one signal that corresponds to at least one maneuver that is similar or identical to one performed with the handle of the surgical instrument;
    at least one haptic feedback device in operable connection to the input device, such that the at least one signal is transmitted to the at least one haptic feedback device;
    a display device operably connected to the haptic feedback device wherein information from the haptic feedback device, including the at least one signal, is transmitted to the display device; and a computer application stored on a computer readable medium and accessible by the display device, that, when executed, generates a virtual model on display device of at least a portion of the surgical instrument working tip, such that the virtual model working tip is similar or identical to one controlled by the surgical instrument handle used an the input device, generates a virtual model in the virtual environment on display device of at least one object that interacts with and is manipulated by the virtual model of the working tip, interprets the information received from the haptic feedback device and modifies at least one of a representation and orientation of at least one of the virtual models displayed on the display device in response thereto, and transmits information back to the haptic feedback device pertaining to the modified display of at least one of the virtual models, where the information causes a haptic response to be transmitted to the input device corresponding to the interaction that caused the modified display of at least one of the virtual models, such that the manipulations of the input device correspond to the maneuvers used to control the surgical instrument and cause a corresponding modification of the display of the one or more virtual models.

8. The system, according to claim 7, wherein the at least one virtual object is an internal organ or tissue.

9. The system, according to claim 7, wherein the input device is the modified handle of an AutoSuture® EndoStitch™ suturing instrument.

10. The system, according to claim 9, wherein the display of the virtual working tip includes at least the upper and lower jaw, and corresponding suturing needle, of the suturing instrument.

11. The system, according to claim 10, wherein the modifications of the display of the virtual working tip correspond to the manipulations of the modified handle that change the position of the jaws or the suturing needle.

12. The system, according to claim 9, wherein the input device comprises a surgical instrument handle modified with at least one microswitch that transmits a signal to the haptic device when the input device is manipulated.

13. The system, according to claim 12, wherein at least one microswitch is utilized to detect at least one manipulation of a sliding lever.

14. The system, according to claim 12, wherein at least one microswitch is utilized to detect at least one manipulation of a handle arm.

15. The system, according to claim 12, wherein the operable connection of the modified handle to the haptic device is by electrical connection.

16. The system, according to claim 12, wherein the electrical connection is facilitated by an electric jack.

17. A method for interactive virtual suturing comprising:
utilizing, as an input device, at least a handle from a surgical suturing instrument modified to generate at least one signal corresponding to at least one maneuver performed with the handle of the surgical suturing instrument and to receive at least one haptic response corresponding to said signal;

operably connecting the input device to a display device such that the at least one signal, generated by manipulating the input device, is transmitted to the display device;

utilizing a computer application stored on a computer readable medium and accessible by the display device, that, when executed, generates a virtual model, on the display device, of at least a portion of the working tip of the surgical suturing instrument, such that the virtual model of the working tip is the similar or identical to that of the surgical suturing instrument working tip utilized as the input device, generates a virtual model, on the display device, of a suture needle that is utilized with the virtual model of the working tip of the surgical suturing instrument, generates, on the display device, an interactive virtual suture by,
determining the location of the virtual suture needle;
associating a first mass point with the virtual suture needle;
generating one or more sequential mass points from the first mass point, with connectivity links therebetween; and
modifying the display of the virtual suture, as the location of the suture needle changes in the virtual environment, by updating the location of sequential mass points based upon the connectivity links, generates a virtual model of at least one object that is manipulated by the virtual model of the surgical suturing instrument and the suture, interprets the at least one signal received from the manipulated input device and modifies at least one of the virtual models displayed on the display device in response thereto, and transmits information to the input device pertaining to the modified display of at least one of the virtual models that causes a haptic response to be sent to the modified handle that corresponds to the modified virtual model displays, such that the manipulations of the modified handle input device correspond to and can cause modification of the display of at least one of the virtual models and where such modification can generate a haptic response to be sent to and be detectable by the modified handle.

18. The method, according to claim 17, wherein the input device is the modified handle of an AutoSuture® EndoStitch™ suturing instrument.

19. The method, according to claim 18, wherein the virtual model of the suture needle corresponds to the AutoSuture® EndoStitch™ suturing instrument needle.

20. The method, according to claim 19, wherein the display of the virtual working tip and suture needle are modified according to the manipulations of the modified handle.

21. The method, according to claim 18, wherein the modified handle of the AutoSuture® EndoStitch™ suturing instrument comprises at least one microswitch that transmits a signal to the haptic device when the handle is manipulated.

22. The method, according to claim 21, wherein at least one microswitch is utilized to detect at least one manipulation of a sliding lever of the AutoSuture® EndoStitch™ suturing instrument.

23. The method, according to claim 21, wherein at least one microswitch is utilized to detect at least one manipulation of a handle arm of the AutoSuture® EndoStitch™ suturing instrument.

24. The method, according to claim 17, wherein the at least one haptic device is a Phantom® Omni™ (SensAble Technologies) haptic device.

25. The method, according to claim 17, further comprising a Follow-the-Leader algorithm to generate the one or more sequential mass points with connectivity links therebetween.

* * * * *